(12) United States Patent
Hope

(10) Patent No.: US 7,819,022 B2  
(45) Date of Patent: Oct. 26, 2010

(54) METHOD AND DEVICE FOR RECORDING CHARACTERISTIC STATE, AMOUNT AND COMPOSITION OF A FLOWING MEDIUM

(75) Inventor: Bjorn R. Hope, Lommedalen (NO)

(73) Assignee: Sensorteknikk AS, Lommedalen (NO)

(*) Notice: Subject to any disclaimer, the term of this patent is extended or adjusted under 35 U.S.C. 154(b) by 53 days.

(21) Appl. No.: 12/293,076

(22) PCT Filed: Mar. 14, 2007

(86) PCT No.: PCT/NO2007/000101

§ 371 (c)(1),  
(2), (4) Date: Sep. 15, 2008

(87) PCT Pub. No.: WO2007/105961

PCT Pub. Date: Sep. 20, 2007

(65) Prior Publication Data

US 2009/0044636 A1    Feb. 19, 2009

(30) Foreign Application Priority Data

Mar. 16, 2006  (NO) .................................. 20061226

(51) Int. Cl.  
*G01F 1/37* (2006.01)

(52) U.S. Cl. .................................................. 73/861.52

(58) Field of Classification Search .............. 73/861.21, 73/861.18, 861.52, 861.22, 861.24, 861.04  
See application file for complete search history.

(56) References Cited

U.S. PATENT DOCUMENTS

| 3,956,928 A | 5/1976 | Barrera | |
|---|---|---|---|
| 5,083,452 A * | 1/1992 | Hope | 73/61.49 |
| 6,651,514 B2 * | 11/2003 | Zanker | 73/861.52 |
| 2004/0000197 A1 | 1/2004 | Bysling | |

FOREIGN PATENT DOCUMENTS

| EP | 0825436 A1 | 2/1998 |
|---|---|---|
| WO | 9604528 A1 | 2/1996 |

* cited by examiner

*Primary Examiner*—Jewel Thompson  
(74) *Attorney, Agent, or Firm*—Volpe and Koenig, P.C.

(57) ABSTRACT

Method and device that by acoustic signal energy—generated by a flowing medium, detects characteristic properties, amounts and the individual distribution between several components/phases, i.e. liquids, gases, particles or any distribution individual and between these. The flowing medium is decided to pass through at least one in a pipe system installed flow conditioner that has at least one restriction and by said passing is decided to release acoustic signal energy. The flow conditioner is installed in such a way that it in an acoustic and/or thermal way is totally or partly isolated from upstream and downstream adjoining sections of the pipe system and/or surrounding construction details.

21 Claims, 3 Drawing Sheets

METHOD AND DEVICE FOR RECORDING CHARACTERISTIC STATE, AMOUNT AND COMPOSITION OF A FLOWING MEDIUM

The present invention concerns continuous registration of a through flowing medium's characteristic state, amount and composition by using acoustic spectroscopy based on passive acoustic, functioning as a continuous, real time analyse of the flowing medium. Such an analyse may be related to e.g. interrelated composition between several components/materials/phases in a flowing medium which again could be fluids, gas, particles or any composition of these, together with possible interrelated composition of each phase.

More specific, the invention concerns a method as mentioned in the ingress of enclosed claim 1 together with a device as mentioned in the ingress of enclosed claim 12.

In the patent literature, e.g. in Norwegian patent No 166379 and No 316343, it is described several methods of registration of a through flowing medium using acoustic principles. These publications describe that a turbulence creating restriction installed between flanges, generates acoustic signals, which assisted by electronic systems, are able to calculate amounts and compositions. Common for these solutions is that the signal detection restriction is steady installed as a unit by flenses coupled with bolts in order to obtain sufficient tightening between the flense plates, and the restriction is therefore an integrated part of a fluid flowing system. It is also shown that a choke device in a valve can be used as a turbulence creating restriction and be used for characterisation of the flowing medium.

However, the measuring result is to a considerable degree affected by various external and partly large acoustic uncontrolled influence, via and from the surrounding constructions details upstream and downstream the restriction device. Such exposures may e.g. be forces partly being mechanical in the form of bend-, push- and strain forces; partly forces released by pressure- and temperature variations in the system. In addition the exposures may be referred to partly strong acoustic and/or wave propagation signals from process equipment, e.g. pumps, valves etc., having a destructive effect on the measuring result.

Partly large deviations in the measuring system's accuracy occur during the measuring process when external exposures change from the time of calibration to a situation of non flow related influences, e.g. in the form of the mechanical coupling between the turbulence creating restriction and those to this installed construction details. This means that the acoustic oscillation properties from the restriction unit may have large and changeable deviations for parameters being decisive for the characterisation/estimation of the flowing medium. Even when calibrating after the installation, so called place calibration, the measuring result may be affected by other process equipment, and thereby create large incorrect measuring results. Such mistakes/changes could be released by thermal forces because of temperature variations in the medium and/or atmosphere surrounding the measuring equipment, which may release strong mechanical push-, strain- and bending forces, which immediately will have a disturbing influence on the flow conditioner or the restriction unit's acoustic properties, and thereby also the measuring result.

The calibration is here made by registration of the acoustic flow signals where a known size of the medium's composition and amount makes a reference. The signal processing is mainly executed by transforming acoustic signals from a time domain to a spectral distribution by using FFT (Fast Fourier Transform) or similar transformations.

Through an after processing based on a statistical signal analysing method, a model is established and used for calculation/prediction of a medium's composition, amount and state. Disturbing effects mentioned above, introduce in this way dominating variables without any correlation to the flowing medium. Even small changes, thermal and/or mechanical in the connections and joints, including joint packing in a piping system, may cause measuring errors regarding changes in amplitude and frequency. Mentioned disturbing effects will also cause lost calibration, i.e. the calibration is unreliable. A measuring result is depended upon a certain range of the signal in respect of amplitude and frequency covered within the range of the calibration model.

Without sufficient isolation of the turbulence-creating device, it is affected by changes in variations in mechanical, acoustic and thermal contact/coupling with surrounding external construction details. The basis for the calibration will then be changed/lost with the consequence that major errors in the measurements may occur. The changes in the acoustic signals that are generated because of a change in the coupling circumstances, meaning non-flow-related acoustic signals, may result in the measuring system being in reality non-operating because the signals lies beyond the calibration model. The acoustic signals in the model, which should be the basis for prediction of the flowing medium, do not have any correlation to the present flowing medium and thereby the measuring result will be useless or result in a greater inadmissible deviation.

According to the present invention known disadvantages and deficiencies of the known devices are avoided and the accuracy of the measuring result is considerably improved.

According to the invention the features of the method described in the characterisation of claim 1 solve this purpose. Further performances of the method appear in the enclosed, secondary patent claims 2-11.

Furthermore, according to the invention the features of the device described in the characterisation of claim 12 solve this purpose.

Avoided is thereby abovementioned disadvantages and shortcomings by known solutions as the medium that is going to be measured is lead to flow through a turbulence creating flow conditioner, which acoustic and mainly mechanical is installed in a way with no contact to surrounding construction details. Thereby is obtained acoustic signals that only represent the flowing medium's properties without being influenced/disturbed by other noise sources. Furthermore is obtained the possibility of a better system calibration, which is not influenced by local and uncontrollable circumstances. This is obtained as mentioned above by the construction of the flow conditioner, i.e. being acoustic isolated and installed pressure tight in a pipe system in relation to the surrounding construction details.

In the following description the word isolation is meant to be related to a known construction detail in the form of a flow conditioner. Because of the way it is installed/coupled it will reduce to a sufficient degree those for the measuring process earlier mentioned destructive influence effects, which in given situations may appear in the coupling between the flow conditioner and surrounding construction details.

The advantage of isolating the flow conditioner acoustic, mechanical and thermal from surrounding construction details (e.g. flenses, pipe couplings etc.) is mainly to avoid loss of calibration which again may cause total break down of the measuring process, and that the isolation device also establish the necessary tightening function in relation to the flowing medium. Mentioned external influences create non-relevant variables and uncontrollable acoustic couplings towards the flow conditioner. In this way the signals are changed/modified so that they no longer fit in a flow related model. By isolation from the surrounding construction details, it is obtained that the information transferring acoustic signals mainly generated by the through flowing properties of the medium, are not suppressed, influenced or disturbed by said construction details. In addition a tightening function is obtained by using said isolation. Likewise is obtained one for said medium's representative temperature for the flow conditioner without being influenced by surrounding temperature changes. As the flow conditioner acoustic, mechanical and thermal is free coupled from mentioned surrounding construction details, a system- or product calibration is obtained that is not influenced or changed by installing or moving and/or other mechanical, acoustic and thermal influences.

A flow conditioner that in this way is isolated against external influences caused by mechanical, acoustic and thermal effects may easily be adapted for various medias, compositions and amounts. This because of, as earlier mentioned, a new way of securing flexible, mechanical/acoustic isolated couplings towards surrounding constructions details or pipe systems/sections, which e.g. includes pipes, valves, pumps or similar. The way this will be explained in the following the present invention makes it possible with mechanical, acoustic and thermal isolation between the flow conditioner and the surrounding construction details such as pipe couplings etc., and will also have a tightening function, i.e. to have packing at the flow conditioner's coupling in the pipe system upstream and downstream in relation to the flow conditioner in order to prevent leakage of the through flowing medium to the pipe system where the flow conditioner is installed. In this way a sufficient isolation of the flow conditioner is obtained to prevent loss of calibration and thereby obtain sufficient accuracy by a continuous on-line analyse together with prediction of the through flowing medium and its composition in order to optimise a process.

In the figure description it is for distinctness purposes described a few simple solutions to obtain said purpose, but it will be understood that this for the invention is non-limited examples, and that a specialist in his art accompanied by the teaching given in accordance with the invention, will be able to provide other solutions to obtain the necessary acoustic isolation effect, either this is made by construction changes, chosen material and/or a combination of these.

The through flowing medium's properties will in this way be able to generate a wide spectre of acoustic vibrations/signals in the flow conditioner, which again with the assistance of one or more acoustic sensors are transformed to electric process able signals. The signals will be analogue scaled and adapted to analogue/digital transforming by use of a suitable signal processing.

By the following signal processing the signals are converted from time domain to frequency domain for following statistical signal analyse. This is executed by using chemometric/multivariate methods to calculate models based on projection of latent data structure. The models are thereby a connection link, a form of calibration, to calculate an unknown size based on a structured signal pattern, presumed the fulfilment of the demand to correlation within a limited range. The acoustic flowing pattern consists mainly of one spectral part in the form of spectral lines. In addition it may be suitable for the calculation that one or more process parameters, such as pressure, pressure difference ($\Delta P$) and temperature(s) are included in the basis calculation. This concerns also the control/verification of the capacity of the model to calculate e.g. temperature based on the acoustic signals via the through flowing medium and in relation to temperature measured via the process parameters directly on the flow conditioner. This indicates the model's ability to predict.

The models constitute thereby the basis of calibration for the following continuous, on-line prediction/measurement of the various measuring values in the through flowing medium of which the models form the basis. The measuring process is mainly continuous because the acoustic signals in digital form are parted in short intervals (registrations) to convert from time to frequency domain. This is mainly done by using a data program, e.g. a Fast Fourier Transformation (FFT). It is therefore registered more or less continuous spectral- and process variables, which by the model coefficients form the basis for the calculation of those for the models relevant measuring results.

To establish a quick response regarding changes in the measuring medium's composition and amount, it may be suitable to use a hard/software signal processor (DSP), and/or a solution where the signal processor is arranged on a few parallel processing processors, so-called multi-core systems. The signal processing may be arranged in a multi-controller unit which controls/manages one or more in parallel processing processors. A continuous and quick updating/processing of registered measuring data is thereby obtained, e.g. also measuring data from many sensor positions. These may in principle be arranged on one flow conditioner and/or on many flow conditioners being through flowed by the same medium. In this way it is possible to execute a parallel processing of the sensor signals from one or more positions on one or more on-line signal analysers, partly extending the basis of measurement to obtain an accurate prediction/measuring result, and partly to be able to use other for the through flowing medium relevant calculation processes, such as cross correlation or similar.

With the present invention it is possible to detect characteristic properties of the through flowing medium when passing through an, from the surroundings, acoustic/mechanical isolated flow conditioner. Acoustic energy signals are thereby released and these signals are characteristic for the through flowing medium regarding its composition, physical properties, flow conditions and amount. By arranging suitable sensors on the flow conditioner, acoustic, wave propagation signals are transformed to electric sensor signals. The sensor signals are further processed by advanced signal analyses in order to have readable information about the through flowing medium's characteristic properties.

An example of the invention's application may be where the medium mainly exists of a gas mixture for continuous analysing of composition and amounts. It may be a gas mixture supplied to a combustion plant, e.g. a gas power station or similar, and where the gases' composition before and after a combustion process should be registered to optimise the process and minimise environmental discharge of gases such as $CO_2$ or similar. A suitable application may also be analysing and registration of amount of gas composition(s) of a flared gas in connection with faking where it is of great interest to know the amount of discharge of the $CO_2$. Abovementioned is meant as an example without being limited to medium, kind of medium or method.

Experiments have shown that $CO_2$ content in a gas medium distinguish especially good in an acoustic spectral composed signal pattern. In connection with a continuous gas analyse, small amounts of various forms of liquid or particles will emerge as clear structures in the signal pattern. During any circumstances it is decisive for the measuring result that the signal pattern, especially the spectral part, is not influenced by non-relevant effects in the form of mechanical, acoustic and thermal influence which is not included in the natural part of the calibration process.

The flow conditioner is designed in a way that makes it possible during through flows to create stable turbulence in form of acoustic broadband signals based on type of medium, amount, composition and temperature. That means generating/transforming of acoustic signal information, which again may be transformed to electric signal by appropriate installed sensors, acoustic coupled to the flow conditioner without influencing its open vibrating/oscillating acoustic properties. The optimal design of the flow conditioner's turbulence creating details is based on empiric obtained results combined with calculated fluid dynamic (Computational Fluid Dynamics (CFD)) modelling together with type of medium and practical installation range of the measuring system. This to obtain a flowing situation through the flow conditioner that is optimal for converting flow related, broad banded, acoustic energy signals isolated from disturbance from external construction details. An important criteria for the turbulence creating design of the flow conditioner, is to obtain a best possible stable converting of flowing parameters to acoustic signals over a greatest possible measuring range. That means to avoid having stepwise change of flowing separating edges and/or unfavourable individual resonance with large amplitude that suppress the flowing relevant energy signals.

With the word isolation from surrounding or connecting construction details is meant preferably acoustic, mechanical and thermal. Likewise is meant that the isolation idea for natural reasons cannot be absolute, but satisfactorily in order to obtain that external influences or disturbances have no influence on the calibration and the obtained measuring result. The isolation shall prevent disturbing effects from the surroundings via the external construction details. This means also that acoustic energy appearing as wave propagated vibrations in the flow conditioner, by this invention, do not leak by coupled to the external construction details or further sections in the pipe system. In this way is avoided the unwanted suppressing and filtering of the acoustic signals.

The flow conditioner is acoustic so designed that flow exited strong resonance within the part of the frequency band appropriated for transfer of flow information, is avoided. Excitation leading to resonance may totally or partly cover the information relevant for characterising the flowing medium and that the signal/noise conditions are affected in an unfavourable way. The flow conditioner is isolated both acoustic as from external mechanical and thermal influence from surrounding construction details or pipe sections. Thereby it is only the signals that appear by the flowing of the medium that are registered and is included in the calculation basis for the flowing medium. The surface of the flow conditioner is adapted for good acoustic coupling to one or more acoustic sensors in a way that these are in an acoustic optimal position in relation to the geometrical design of the flow conditioner.

As additional variables to the acoustic part of the flow conditioner, pressure, pressure difference and temperature may be measured to secure a better measuring result by including these process parameters in the calibration model. Likewise is established a quality assurance of the model by a direct comparison of the temperature measurement on the flow conditioner with the indirect way of acoustic signals measuring the temperature of mentioned medium.

The acoustic signals generated by the turbulence creating means are mainly related to the mechanical design of the flow conditioner and in a minor way related to the composition of the through flowing medium. As an additional function it may be suitable supplying the flow conditioner with an acoustic excitation/stimulation in the form of a wave propagation signal received by the acoustic sensors and appropriated signal transmission with the following signal process devices. Such stimulation may be in the form of a wave transmitting impulse putting the flow conditioner in a self-vibration pattern, partly for a control of sufficient isolation/uncoupling of the flow conditioner from the surroundings, partly a simple form of after calibration/control of as well the flow conditioner's acoustic properties with or without through flows, as a function control of all procedures in the measuring- and signal process. A signal generator trigging to release an acoustic mechanical excitation signal on the surface of the flow conditioner controls such activation.

Such a stimulation signal may also have any form of character in form of pulses, frequencies and amplitude modulation to generate acoustic wave transmitting signals in the flow conditioner as a condition of state control of its properties. Deviation in the signal conditioner's response regarding external stimulation may be a warning signal that the isolation effects more og less have changed. This may be as a consequence of clogging, incrustation, wear effects, leakage or other conditions that influence calibration and the measuring result. Such a method for remote control of the measuring system's functionality is especially suitable where a manual control is impossible due to practical conditions. This may e.g. be by installation in explosive ranges or in connection with subsea installation or well pit installation.

The flow conditioner may preferably be designed to suit a measuring situation regarding size and design. Likewise it may be preferably that it is equipped with a changeable turbulence creating device adapted in size and design to mentioned measuring medium's amount and composition, temperature and pressure. The device may easily be adapted to said medium, e.g. by material being resistant to erosion or other conditions being favourable in the measuring process and/or medium. The flow conditioner should be designed to avoid local incrustation, erosion contributing to change the acoustic properties and the basis of calibration.

Some times a better characterising of the medium's condition may be obtained by having one or more flow conditioners arranged in series in the flowing direction in order to get a broader acoustic signal basis, partly because of obtained mixing effect, partly because the medium is exposed for a multi step flowing condition.

All comparable flow measurement systems using flow conditioners have generally limited and calibrated measuring ranges regarding amounts and the medium's composition (gas, fluid). In order to obtain greater measuring capability covering a large measuring range, it is suitable to use a manifold system in order to distribute the flow in several parallel flow measuring paths, optimal adapted to each flow conditioner's measuring range/calibration. Using a system consisting of valves and measuring paths, the measuring ranges may be distributed in two or more parallel arranged flow conditioners. Each of these may have the same measuring range/ measuring capability or different measuring range/measuring capability. This means that the total flow represents the total amount of each medium flowing through the activated flow conditioners. This is to obtain maximum flexibility regarding mentioned measurement of the medium's flow rate and composition. Likewise is obtained with such a parallel activation and deactivation of the flow conditioners, a redundant effect being especially useful in connection with remote controlled subsea or down hole installations. In addition is the calibration process simplified in situations where calibration, because of capacity reasons, is difficult or impossible to perform and where each phase may differ over a large range.

The acoustic signals are converted into electric signals by using one or more sensors. The signal processing after the conversion to digital form with following signal analyses, is performed by a transformation from a time related signal (time domain) to a signal in spectral form (frequency domain).

By using statistical signal analysis, "Principal Component Analyses" (PCA) and Partial Least Squares (PLS), a regression model is calculated using known methods. Within the regression model is concentrated all relevant information for the following calculation/prediction of the flowing medium based on continuously registered measuring data. Normally the measuring range is limited to the original calibration process as well regarding to the extent of each measuring parameter as the measuring range making the basis for the calibration. In order to make the regression model function within said range, it is assumed that the measuring parameters included in the model are not disturbed or influenced by conditions not relevant for the flowing medium's calibration range.

The invention aims to solve the problem with external disturbance that totally or partly cause the calibration to be out of function as described above. The method including use of so-called multivariate calibration to establish a PLS model for prediction of a new data set having a changeable range within the model is well established and known. Reference is made to various descriptions of multivariate calibration and chemometric methods: "Multivariate Calibration" by Harald Martens, Svante Wold and Kim H. Esbensen.

The invention also describes a solution that enables extrapolation or extension of the measuring range for registered measuring parameters beyond the range of the calibration model. This on the understanding that the acoustic signals being registered are not influenced by external disturbance, and that the signals release information only relates to the flowing medium. A new model with extended measuring range is calculated from a number of partial models within the calibration model. This means that the same function with which the range dependent variables are changed within the calibration model is used to calculate the new extended model, which measuring range covers the calibration model.

The following figures show how the invention is feasible in the form of practical solutions. The described solutions are in no way limited for the invention as to how the acoustic isolation effect is obtained or how the practical implementation is made.

Figure 1:
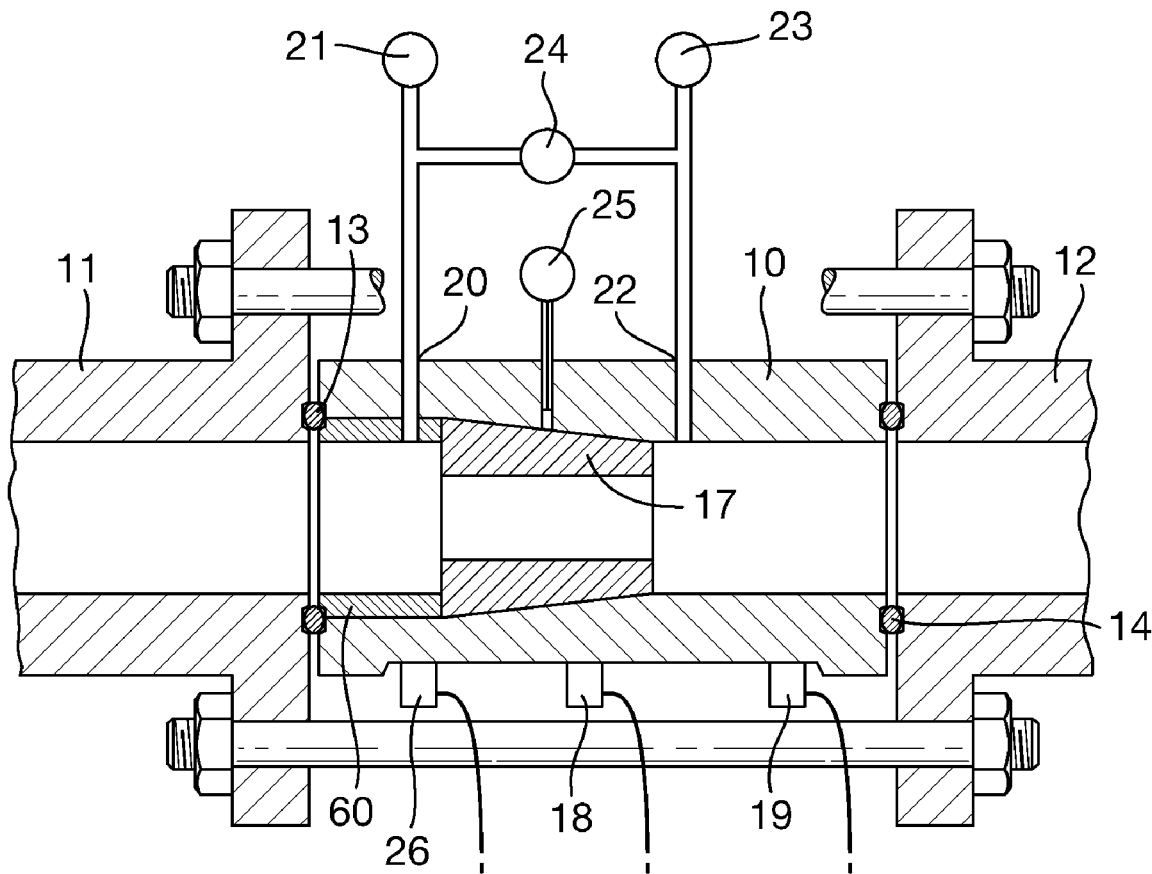
FIG. 1 shows an example of isolation of the flow conditioner.
Figure 3:
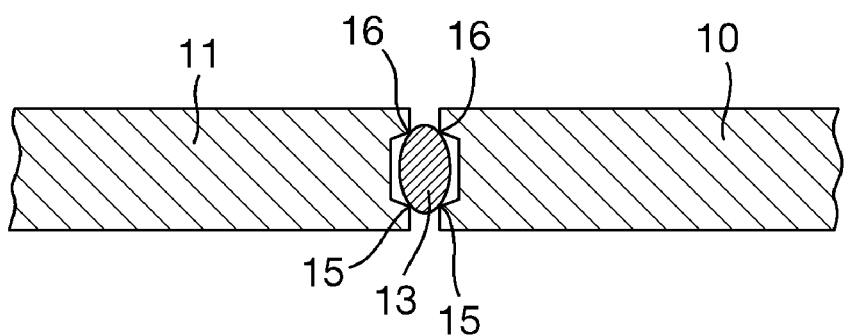
FIG. 3 shows a cut-out of a packing steel ring between a pipe system and the flow conditioner.

In FIG. 1 is shown a method for installing a flow conditioner 10 directly in a pipe system 11, 12 where the acoustic isolation effect is combined directly with packing devices 13, 14. The gasket device may be a steal ring or other suitable tightening material means. As shown in FIGS. 3, 15, 16, the isolation effect is obtained only by minor contact between the rings 13,14 and the flow conditioner 10 on one side and the pipe system 11, 12 on the other side being hold together by a system of flenses and bolts (as suggested in FIG. 2), without influencing the acoustic properties of the flow conditioner. The material choice in the rings 13, 14 may furthermore give a thermal isolating effect limiting the thermal coupling between the flow conditioner and surrounding construction details.

Figure 2:
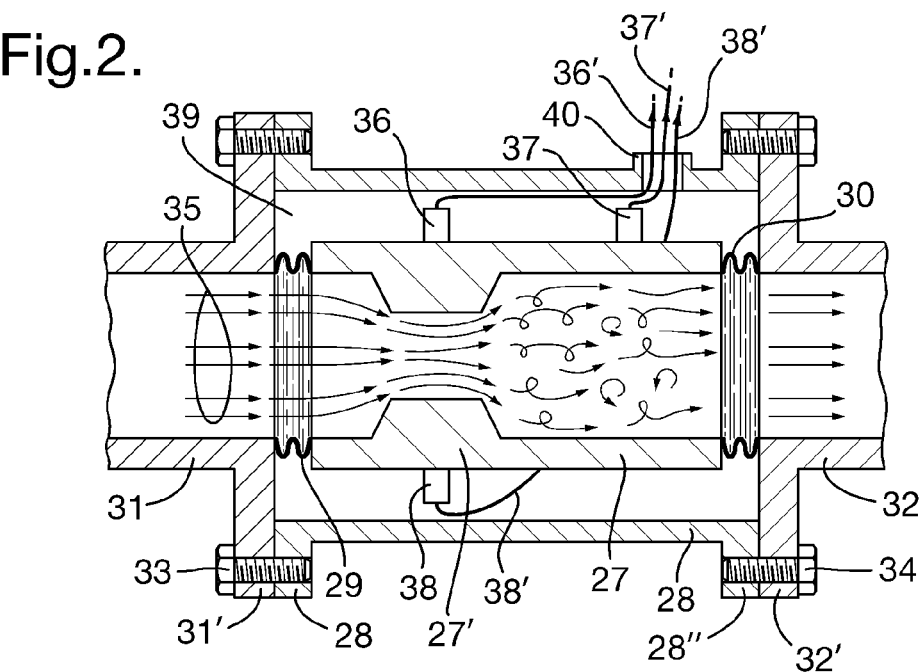
FIG. 2 shows an example of an installed device of an isolated arranged flow conditioner.

In FIG. 3 is shown a cut-out from FIG. 1 as to how the acoustic and thermal isolation may be established by using mentioned rings 13, 14. The isolation and tightening may be included through the way the tightening is established using a know method, and that this method also establish an acoustic wave propagation isolation to prevent/limit the influence from/via the surrounding construction details 11 to the flow conditioner 10. Complete tightening is obtained via the ring 13 via contact points 15,16. To obtain a greater isolation effect, two or more of mentioned gasket devices may be coupled in series, but this is not shown in the figures. The choice of material in these gasket devices may furthermore contribute to reduce the acoustic, mechanical and thermal coupling in relation to external construction details consisting of coupled pipes and flange arrangements. A complete tightening is obtained when the flow conditioner 10 is installed between external construction details with flanges and longitudinal bolts or as shown in FIG. 2 through an installing device 28 and in a way that prevent forces of installation couplings or variations of these to be transferred to the flow conditioner.

In FIG. 1 is shown a flow conditioner 10 with a changeable restricted and turbulence created part 17 forced in a flow conditioner 10. Thereby is obtained as shown in the example both a good fixing as acoustic and thermal contact between the turbulence creating part 17 and the flow conditioner 10 because the contact surfaces between these are slightly conic. A further security device to obtain that the turbulence creating part 17 is steady, may be done by a fastening device 60 that simultaneously works as a dimension adapter for upstream inlet. Other installation methods to get the same effect may as an example be based on at least one of: Glueing, soldering, welding and screw fixing via the flow conditioner 10.

This solution enables an adaptation to various amounts of and/or properties to a medium. It could also be suitable to choose a high quality material for the flow conditioner to prevent or reduce erosion or other form of flowing wear, which again may influence or change the flow conditioner's acoustic properties. Installation of part 17 in the flow conditioner 10 is made by establishing a good acoustic contact surface, as an example using a conic fastening device, so that the changing between various sizes do not change the calibration at each applications. The acoustic signals from the flow conditioner are registered via one or more sensors 18, 19 placed on the surface of the flow conditioner.

FIG. 1 shows the possibility of installing further sensors to measure the additional parameters that could be suitable to install on the flow conditioner and near the turbulence creating part 17. As an example a pressure outlet port for a pressure gauge/sensor 21 is installed to measure the pressure P1 upstream in relation to the flow conditioner. In addition it is installed an outlet port 22 to measure the downstream pressure P2 using a pressure gauge/sensor 23, and the possibility of measuring the pressure difference (P1-P2) using a differential pressure gauge/sensor 24. Temperature T in the flow conditioner 10 may, by using a temperature gauge/sensor 25, be registered in order to obtain an optimal repetition of the flowing medium's temperature. In addition it may be suitable to install a mechanical/acoustic signal transducer 26 on the flow conditioner 10.

In FIG. 2 is shown another design of the flow conditioner, here mentioned 27, attached in an installing device 28 and acoustic, mechanical and thermal isolated using mechanical flexible suspended devices 29, 30. The turbulence creating part of the unit 27 is mentioned with 27'. These devices 29, 30 is so designed that mechanical, acoustic and thermal isolation between the flow conditioner 27 and the installing device 28 is obtained, and the installing device 28 may be connected to a pipe arrangement 31, 32 for example via flange connections 28', 31'; 28", 32' fixed with bolts 33, 34 as shown on the figure, or using other suitable know couplings.

The medium 35 flows in and through the turbulence creating part of the flow conditioner 27' having a design adapted to the flow rate and amount and type of medium. In addition is established a stable flowing profile of the total measuring range. The flow conditioner 27 may be equipped with one or more acoustic sensors 36, 37 separated from the flowing medium, for example on the outside of the flow conditioner 27 in a clearance space 39 between the installation device 28 and the flow conditioner 27. Signal cables 36', 37' from the sensors 36, 37 may be led out via a tightening cable transition 40. Likewise may a signal cable 38' be led via the cable transition 40 to an excitation transducer 38, equivalent to the transducer 26 in FIG. 1.

In addition it is suitable to use additional sensors to register pressure, pressure difference and temperature as additional parameters. These sensors may be arranged either on the isolated flow conditioner 27 or in connection with the surrounding construction part. The arrangement of such extra sensors (not shown on the figures) will be obvious for an expert skilled in the art. In a practical design the outlets for measuring pressure and temperature may be arranged in connection with the surrounding external construction details 31, 32, preferable close to the flow conditioner 27. It is undoubtedly an advantage that the pressure and temperature measurements are made close to the flow conditioning and turbulence creating unit 17 (FIG. 1); 27 (FIG. 2). This means that the process- and the acoustic measuring parameters should be collected simultaneously.

The flow conditioner 17; 27 may have different designs depended upon the medium that is measured and surrounding systems. The optimal design of the flow conditioner may for example be based on empiric obtained results, combined with calculable fluid dynamic (Computational Fluid Dynamics (CFD)) modelling. This is made in order to obtain a flow situation through the flow conditioner being optimal for conversion of flow related broad banded acoustic signals isolated from external constructions related disturbances. With isolation from surrounding construction details is meant acoustic and mechanical release in relation to wave propagation signals having a disturbing influence on the measuring process. With thermal isolation is meant that temperature measurements on a flow conditioner is representative for the flowing medium 35 and is not thermal influenced by conduction, convection or any other way from the external construction details.

When the flow conditioner is installed vertically, no problems occur in connection with liquid flowing upstream on and off. The flowing medium is then homogeneous during a measuring period. However, it is suitable because of the pipe system, especially concerning large dimensions, that the flow conditioner also has a horizontal or closer to horizontal than vertical position.

As an example: In cases where especially the amount of gas in a flowing medium is high (90-99%) and the liquid part in mentioned medium is accordingly low, the liquid part will move as a liquid film along the pipe wall and may, when meeting the restriction in the flow conditioner create local liquid storage. This will then, independent of the flowing conditions create relatively large liquid parts, which now and then and irregularly will pass and cause large changes in the acoustic signal which are not representative for an average and normal stable flow situation in for example a wet gas pipeline.

By using advanced algorithms such effects may possibly be compensated for, but because this is an uncertain and unstable situation, it is according to the invention proposed to introduce longitudinal channels in the restriction part of the flow conditioner. This has been found to be a suitable solution. Such longitudinal channels have no influence on the importance to transfer the flow to acoustic information, especially when the effect is included in the calibration procedures.

The flow conditioner may also function as a medium mixer contributing to homogenisation of the flowing medium consisting of components, phases; mixing liquids etc. Preferably is the flow conditioner installed mainly in vertical flow direction. In cases where the flow conditioner is installed horizontally or almost horizontally, the measuring result will be influenced of local flow effects being created because local liquid storage is built up close to the turbulence creating restriction, which again creates unstable flow situations that solely are local and construction related and therefore not representative for the flowing medium's composition and amount. Minor variations in the flowing medium's composition and amount is decisive for how mentioned effects behave and thereby create major problems in connection with calibration and the measuring process. When local generated minor liquid plugs occur in the flowing medium, large variations are created in the acoustic signal, as well in amplitude as spectrally.

Because the turbulence creating restriction is performed with longitudinal draining channels in the flowing direction, such local liquid storage is prevented preferably on the upstream side. In this way the measuring accuracy of the sensor system is independent of the direction in which the system is installed.

Figure 6:
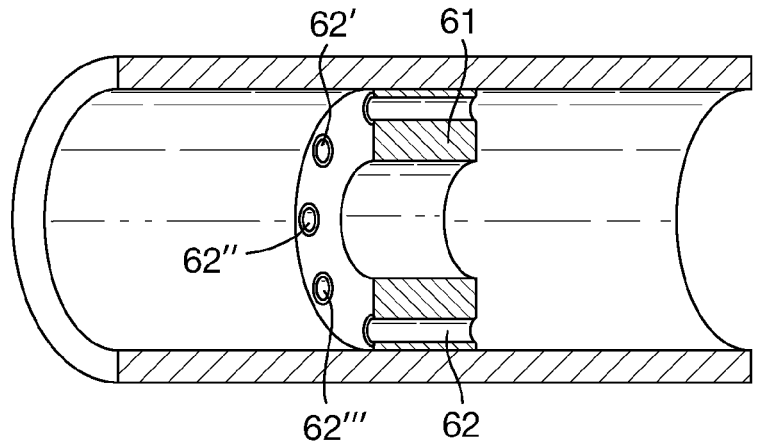
FIG. 6 shows a design of a turbulence creating restriction with cylindrical draining channels.
Figure 7:
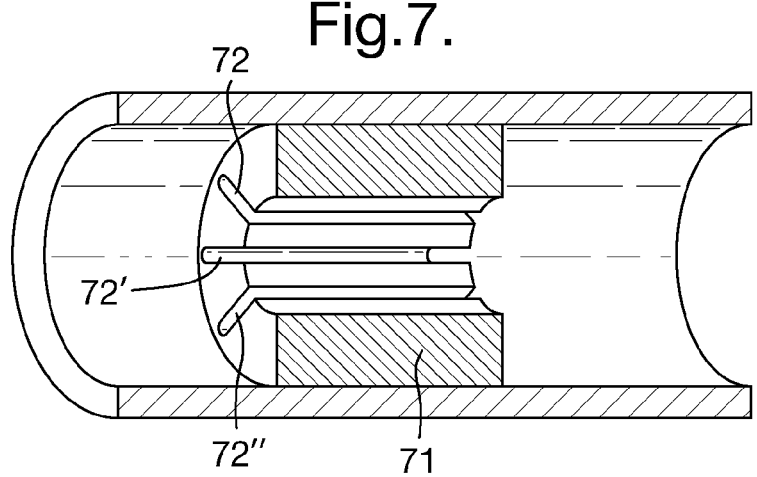
FIG. 7 shows a design of a turbulence creating restriction with longitudinal, open and slotted draining channels.

In FIGS. 6 and 7 are shown examples of draining channels that could be in form of longitudinal tubular channels 62-62''' in the material of the restriction 61, or slotted open channels 72-72" in the material of the restriction 71 close to its outer wall and distributed along the perimeter in a way that sufficient draining is secured during all thinkable installation positions. As shown in FIG. 6 (by the channels' in- and outlet) and in FIG. 7, the channels may preferably have a hydrodynamic design to prevent the creation of incrustation/clogging and prevent or limit local turbulences at the channels. Those in FIGS. 6 and 7 shown examples of draining channels are however not limited to the shown geometric performances in connection with the turbulence creating restriction.

The draining channels will especially be advantageous to use when at least one medium that are measured is a liquid, for example condensate, oil, water, salt water, particles mixed in liquid and/or gas phase or various mixings of two or more of these.

Figure 4:
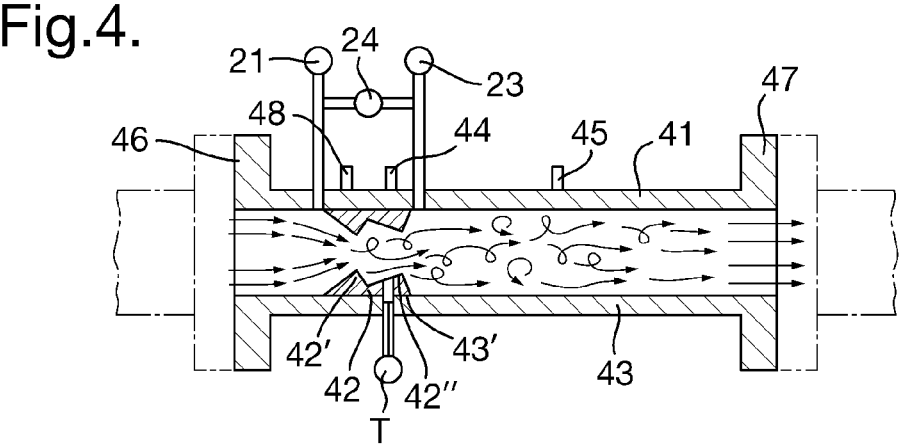
FIG. 4 shows a flow conditioner solution in the form of a device in a pipe system.

In FIG. 4 is shown an alternative solution of a flow conditioner 41 in form of a flow-conditioning device 42 in a pipe section piece 43. The turbulence creating part 42 is as an example designed as two restrictions 42', 42" in series and have good acoustic and thermal contact to the pipe section's 43 inner surface 43' so that the sensors 44, 45 are acoustic and mechanical coupled to the device 42. The isolating effect in this case is obtained mainly by a comparatively large distant between the flow conditioner device and the attachment/flanging towards a pipe/transport system as mentioned by 46, 47. Because of a radial distribution of the flow related acoustic signals, an intended isolation effect/reduction in the pipe section's 43 length direction is obtained, partly because the distance to the attachments of the sections upstream and downstream are relatively much longer than the diameter. Choice of material and possible mechanical construction details will establish further isolation effect to avoid disturbing effects from surrounding constructions.

In the figure is also shown an acoustic/mechanical excitation transducer 48 being suitable for a function control of all parts in the measuring- and signal processing means. Likewise is an active stimulation of a flow conditioner a control that the isolation effect is being maintained. Through an impulse stimulation from the transducer 48 the flow conditioner's 41 part 42 will react with an oscillation pattern being characteristic for the flow conditioners condition regarding isolation, wear or other errors. The same way as shown in FIG. 1 the P1 and P2 pressures are measured upstream and downstream in relation to the turbulence creating part 42 in the flow conditioner 41 together with temperature. The pressure difference dP is registered via the same outlet ports as P1 and P2 and the measuring may be performed with the pressure sensors 21, 23 and 24 as also shown in FIG. 1.

FIG. 1 shows in details how the pipe section 11, 12 may be attached to the pipe section or flow conditioner 10. This may also be performed by using a surrounding cover or construction detail 28 as shown in FIG. 2 with appropriated flanges such as the flanges 28', 28" in cooperation with flanges 31', 32' on the pipe sections 31 and 32. A similar solution may be used in FIG. 4. Either by using transition elements 13, 14 as shown in FIGS. 1 and 2 or by using elastic elements 29, 30 as shown in FIG. 2. In FIG. 4 is shown, as an example, by broken line how the pipe sections may be attached to the flow conditioner.

Figure 5:
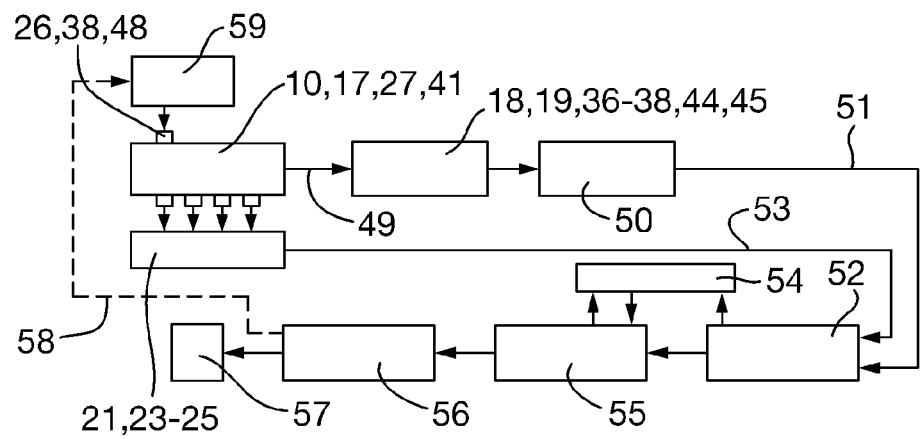
FIG. 5 shows a block diagram of the signal route from the flow conditioner as a generator via signal processing to a final measuring result.

In FIG. 5 is shown a block diagram with the flow conditioners 10; 17; 27; 41. Acoustic energy signals 49 are registered via the sensors 18, 19; 36-38; 44, 45 and are transferred to the following signal analyser 50 where an analysing result is processed mainly in the form of a signal spectre 51. In a module 52 the signals 53 from the process sensors 21, 23-25 and the signals 51 representing the acoustic spectre, are being coordinated and synchronized in time. In this way the signals are saved and propositioned for calibration in the module 52. In a calculation module 54 is made a calculation process forming the basis for a measuring range extension based on as well saved data in the module 52 as data in a module 55 for statistical analysis.

On the figure is shown a stippled control connection 58 to a signal generator 59 for releasing of acoustic, mechanical related signals via acoustic transducers 26, 38, 48 to the flow conditioner. In this way a simple and useful function test of the whole system with or without through flowing of a medium may be performed. Using the signal generator 59 and an acoustic, mechanical related signal transducer 26, 38, 48 in connection with a function test or calibration, a signal procedure of different and suitable character might be applied. It could be a combination of constant and/or variable frequencies with constant and/or variable amplitudes. The signals may consist of a complex composed signal procedure being characteristic for the flowing medium during different flow conditions. In addition this will function as a condition control of the flow conditioner regarding changes in acoustic response during the excitation of the transducers 26, 38, 48. As an example this function is a useful tool for an investigation of internal condition wear/erosion and/or clogging/incrustations. Such conditions have an impact on the signal conditioner's natural vibration/oscillating properties. Another example is a function test of the acoustic sensors 18, 19, 36-38, 44, 45 and the sensors' acoustic coupling to the flow conditioner.

A calibration executed within a limited measuring range regarding amount and/or composition of a flowing medium, form the basis for the establishment of another, preferably extended measuring range by extrapolating of a selection of the most significant signal variables representing a linear or close to linear relation between the acoustic energy signals and the medium's composition and amount. The calibration process ends up with one or more models being saved in a model database 56.

Continuous prediction of the flowing medium is therefore made based on continuous registered acoustic signals related to measured spectre and process data and that for the measuring range relevant model. In a reading unit 57 the measuring data is adapted to one for the user suitable way, for example in form of a visual presentation and/or a continuous logging of the measuring results.

Figure 8:
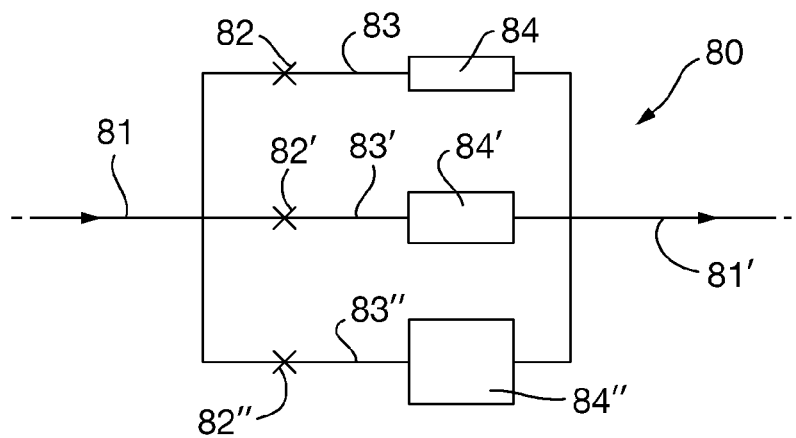
FIG. 8 shows how a main flow stream may be divided in at least two parallel flow stream paths with a flow conditioner in each path to obtain a maximal flexibility regarding measuring capability and measuring range.

In FIG. 8 is shown a manifold system 80 in order to divide the main flow route 81 in at least two parallel flow routes. In this example is chosen three parallel flow routes 83, 83', 83", but two or more than three flow routes are of course possible. The valves 82, 82', 82" enable selective coupling of one of the flow routes 83, 83', 83" to respective flow conditioners 84, 84', 84". These flow conditioners could all be of same type or of different type, chosen for example from the types mentioned with 10 in FIGS. 1, 27 in FIG. 2 and 41 in FIG. 4. The flow transfer routes 83, 83' and 83" is collected downstream to a common main stream route 81'. Each part stream is calculated separately as earlier described. By a combination of opening or closing the valves 82, 82', 82" of the respective transfer routes 83, 83', 83", an optimal utilization of the respective flow conditioners' measuring ranges/measuring ability is obtained. This is an advantage related both to variation in medium amount per flow rate and the composition of mentioned measuring medium. Another advantage related to the transfer routes is that the measuring could take place in the most suitable part of the respective flow conditioner's measuring range, which also means that each and a combination of transfer route will have a certain redundant measuring range/measuring ability.

Even if the shown solution at the same time is using at least two of the parallel coupled flow conditioners, it is of course possible to use one flow conditioner at a time, especially if the flow conditioners are of different types or best suited to measure within various measuring ranges or best suited to measure special types of mediums or composition of several types of mediums.

By the present invention is therefore, by using acoustic signal energy generated by a flowing medium, registered mentioned medium's characteristic composition, amounts and the interrelated distribution between several component/phases included in said medium, for example liquids, gases, particles or any distribution amongst them. The invention distinguishes itself by the flow conditioner causing the generation of the flow related acoustic signals. The flow conditioner as earlier mentioned, is installed pressure tight and mechanical, acoustic and thermal isolated from the external construction details. This means that all non-flow-related influences from surrounding construction details in a pipe/transport system has no impact on the flow conditioner's acoustic properties.

The turbulence creating flow conditioner is as mentioned before isolated from the external construction details regarding generation of acoustic energy signals and thereby prevent the acoustic energy signals via the flow conditioner from being influenced by non-flow-related, disturbing effects being one or more of the following: Acoustic and/or other wave propagation energy signal from other signal sources, variations in mechanical couplings, compression/tensile and bending forces via external construction details, surrounding temperatures that are not related to a medium, and temperature variations that are not related to a medium.

By having established one or more suitable attachment points for acoustic sensors on the surface of the flow conditioner and possible on suitable positions upstream or downstream the flow conditioner, these sensors will have an approximately acoustic loss free coupling to the flow conditioner.

It could thus be understood that integrated in the flow conditioner could be registered additional information or additional parameters related to the flowing medium in the form of upstream or downstream pressure, pressure difference and temperatures combined or individual as additional variables in connection with the calculation of a model or by prediction. Furthermore is established a mechanical, acoustic and thermal isolation between the flow conditioner and the external construction details, which have a tightening function between the flow conditioner and the external construction details and prevent leakage of the medium. The flow conditioner's inner construction details has a suitable flow performance, chosen out of composition and amount per flow rate of said medium, causing that no erratic change occurs regarding the generated medium turbulence as a consequence of the cooperation between the flow conditioner and said medium, by, as an example that the dominating part of the turbulence change erratic between front and end of the turbulence creating restriction.

The flow conditioner may be performed with a changeable, acoustic turbulence creating device made of a, in relation to said measuring medium's resistive material, meaning that mentioned material is not influenced or changes as a consequence of the through flow of said medium. In order to prevent that local flow situations arise that cause incrustation, the transfers between the flow conditioner and its turbulence creating restriction are so executed that no sharp angles are created.

In connection with the flow conditioning a certain mixing effect is obtained with the additional purpose to homogenise mentioned measuring medium to obtain a stable and for the flowing medium representative acoustic signal information. One or more flow conditioners may be individual acoustic isolated and arranged in series in the flowing direction in order to obtain a broader acoustic signal basis, partly because of obtained mixing effect, partly as a consequence of mentioned medium being exposed for a multi-stage treatment. Furthermore it is possible to imagine that the flowing medium may be distributed on one or more individual and in parallel arranged flow conditioner devices.

Through acoustic, mechanical, thermal release or isolation of the flow conditioner, the original calibration is not affected by changes or moving to another measuring position. A calibration made within a limited measuring range regarding amount and composition of the flowing medium, forms the basis for establishing another, preferably extended measuring range by extrapolation of a selection of the most significant signal variables that represent a linear or close to linear relation between the acoustic energy signals and the composition and amount of the medium. On the flow conditioner may as earlier mentioned be installed an excitation device by using a wave propagation signal transducer, acoustic/mechanical, in order to obtain an additional function for calibration/function test of the flow conditioner with or via the acoustic sensors and corresponding signal transfers and signal processing devices.

The signal processing of the acoustic signals is being processed parallel from one or more sensors and/or by using one or more signal processors to obtain a continuous measuring situation also where large and fast phase- and amount changes arise in the flowing medium, as an example this could be various forms of slug or plug related flows.

In connection with a preferred, but for the invention not limited design, the mentioned medium could for example consist of mainly gases for a continuous direct analysis and flow metering of each fractions and compositions, also including environmental gases as $CO_2$ or similar. Particles in mentioned flowing medium, for example sand or similar will create significant acoustic signals and in this way establish a way for sand detection and/or flow metering. Particles registered in the flowing medium are different from liquid- and gas related signals. The signals generated from sand particles in liquid or gas or a mixture of these, emerge as a characteristic high frequent signal pattern that clearly differs from other flow related acoustic signals. The system is in principle also suited to detect sand rates in a flowing medium.

According to the invention a model may be established for extended measuring range beyond the original calibration model and thereby establish the basis for a continuous prediction/measuring of a flow medium's composition, amount, pressure and thermal properties.

The invention claimed is:

1. A method to register a flowing medium's characteristic features or properties, where the flowing medium being intended to pass through at least one flow conditioner installed in a pipe system, said flow conditioner having at least one flow restriction which upon said passing of the flowing medium through the restriction is configured to release, for signal processing, flow related acoustic signal energy being representative of said characteristic features or properties, and detecting said acoustic signal energy for signal processing and analysis, the method comprising:

installing said flow conditioner in or as a structural part of the pipe system so that it is acoustically isolated from upstream and downstream sections or constructions of the pipe system, and detecting and processing from the flow conditioner in said structural part the flow-related acoustic signal energy from said medium as it passes through the flow conditioner without influence from, any non-flow related disturbing signal effects present in said upstream and downstream sections or constructions of the pipe system.

2. The method according to claim 1, further comprising installation of the flow conditioner so that it is at least one of acoustically or thermally isolated from a cover or construction detail surrounding the flow conditioner.

3. The method according to claim 1, further comprising determination at the flow conditioner at least one of:

a) flow rate of the medium measured as a function of differential pressure between inlet and outlet of the flow conditioner;
b) flow pressure of the medium inside the restriction of flow conditioner;
c) condition phases of the medium as a function of measured acoustic energy, and
d) mutual distribution of at least two components of the medium, said medium being at least one of liquid, gas and particles.

4. The method according to claim 1, the non-flowing-related disturbing effects comprising at least one of:
acoustic or other wave propagation energy signal from signal sources other than provided by use of said flow conditioner, and
variations in mechanical coupling or bending forces via external construction details.

5. The method according to claim 1, further comprising using a pipe manifold arrangement comprising a plurality of parallel pipe branches branched off at an upstream end from a main flow pipe section and at a downstream end merging into a downstream main flow pipe section, each branch having a flow conditioner, wherein said medium is routed from upstream main flow section and from there is:
selectively routed in and through a flow conditioner in one of said plurality of pipe branches,
or selectively routed with a respective part of the medium flow through a flow conditioner in a respective one of at least two of said plurality of pipe branches.

6. The method according to claim 1, wherein:
the detection and signal processing or signal analysis is executed as a calibration of the flow conditioner,
the calibration is made within a defined measurement range as a function of at least one of the following parameters:
a) passing medium flow per unit time through the flow conditioner,
b) the composition of said flowing medium,
c) a selection of the most significant signal variables representing a linear or close to a linear relationship between the acoustic energy signal and at least one of the composition or flow rate of said medium.

7. The method according to claim 6, wherein from one point on the flow conditioner is sent an acoustic excitation signal from an acoustic/mechanical wave propagation signal transducer for at least one of additional calibration or function testing of the flow conditioner with and via the acoustic sensors and the following said signal analysis.

8. The method according to claim 1, further comprising performing signal processing of signals from the detected flow-related acoustic signal energy, said signal processing performed in parallel from at least two sensors using one or more signal processors in order to obtain a continuous measurement.

9. The method according to claim 1, wherein by detection is established an additional model for extended measuring range beyond an established calibration model, as the additional model forms the basis for a continuous prediction or measurement of a flowing medium's composition, flow rate, pressure and thermal properties.

10. A device to register a flowing medium's characteristic features or properties, where the flowing medium being intended to pass through at least one flow conditioner installed in a pipe system,
said flow conditioner having at least one flow restriction which upon said passing of the flowing medium is configured to release flow related acoustic signal energy detectable by at least one acoustic signal sensor and to be processed by a signal processor connected to at said at least one sensor, said flow related acoustic signal energy being representative of said characteristic features or properties,
wherein the flow conditioner is installed in or as a structural part of the pipe system, wherein the flow conditioner is at least partly acoustically isolated from upstream and downstream adjoining pipe sections or constructions of the pipe system,
wherein said acoustic isolation is provided by at least one of:
at least one elastic or flexible element between ends of the flow conditioner or its structural part and said upstream and downstream adjoining sections or constructions of the pipe system, and
reduced contact region between ends of the flow conditioner or its structural part and said upstream and downstream adjoining sections or constructions of the pipe system, said contact region being a fraction of end flanges on said selections or constructions, and
wherein at least one acoustic sensors are installed onto an outside face of the flow conditioner or said structural part.

11. The device according to claim 10, wherein upstream, downstream and differential pressures of the flowing medium communicate via pressure lines with ports located upstream and downstream of the restriction, wherein pressure sensors related to measuring said upstream, downstream and differential pressures are connected to said signal processor and to respective ones of said ports, said differential pressure sensor being connected to the ports located upstream and downstream of the restriction, a temperature sensor is installed partly through the wall of the pipe section or flow conditioner in direct or indirect thermal contact with the through flowing medium.

12. The device according to claim 10, wherein an acoustic transducer is arranged on an outside face of said flow conditioner or said structural part upstream of said restriction, in order, by activating the transducer, to perform at least one of a calibration or function test of the flow conditioner, said acoustic sensor(s) and said signal processor.

13. The device according to claim 10, further comprising a pipe cover or construction detail surrounding said flow conditioner or structural part, said cover exhibiting an inner diameter that is larger than an outer diameter of said flow conditioner or structural part, the pipe cover or construction detail at each end being mechanically and pressure tight connected to a respective adjacent end of a section or construction of the pipe system, and wherein a space thus created between the exterior of said flow conditioner or structural part, and an inside face of the pipe cover or structural detail being pressure and mechanically isolated from a medium caused to flow in the pipe system and through said restriction of the flow conditioner.

14. The device according to claim 10, wherein the flow conditioner has a restricted, central flow channel into which a turbulence creating part of the flow conditioner is placed in a replaceable manner, and wherein the turbulence creating part is made from a material, which is resistant to wear, causable by the flowing medium.

15. The device according to claim 10, wherein said flow restriction in said flow conditioner comprises, between an inlet and an outlet thereof, at least one curved or bevelled, said curved or bevelled configuration in order to prevent incrustation or clogging.

16. The device according to claim 10, wherein the flow conditioner has a main flow, centrally located, axial passage therethrough and parallel tubular or open slotted draining channels located radially between said passage and an exterior face of the flow conditioner and wherein said channels are operative to prevent or limit that changes in the acoustic energy signals occur due to local storage of said medium in any situation where the flowing direction of the medium deviates from a substantially vertical direction.

17. The device according to claim 10, further comprising a plurality of mutually acoustically isolated flow conditioners arranged in respective parallel branches of a manifold system each branch providing a respective, selectively operable medium flow route through use of a controllable valve in the respective branch to provide for said medium to be able to flow through a selected one of said flow conditioners or with a respective part of the medium to flow through at least two respective ones of said plurality of flow conditioners.

18. The method according to claim 1, further comprising thermally isolating the flow conditioner from said upstream and downstream sections or constructions of the pipe system, and wherein the non-flow related disturbing effects comprise at least one of:

surrounding temperatures that are not related to the flowing medium; and temperature variations that are not related to the flowing medium.

19. The device according to claim 10, wherein said acoustical isolation of the flow conditioner also provides for thermal isolation.

20. The device according to claim 19, wherein the flow conditioner or structural part is thermally isolated from the cover or construction detail surrounding the flow conditioner.

21. The device according to claim 13, wherein the flow conditioner or structural part is thermally isolated from the cover or construction detail surrounding the flow conditioner.

* * * * *